United States Patent [19]

Petusky

[11] Plant 4,478

[45] Nov. 6, 1979

[54] CHRYSANTHEMUM NAMED RUFFLED SPIRIT

[75] Inventor: Kerry S. Petusky, West Chicago, Ill.

[73] Assignee: Pan-American Plant Company, West Chicago, Ill.

[21] Appl. No.: 964,435

[22] Filed: Nov. 28, 1978

[51] Int. Cl.[2] ..... A01H 5/00

[52] U.S. Cl. ..... Plt./77

[58] Field of Search ..... Plt./77

*Primary Examiner*—Robert E. Bagwill

*Attorney, Agent, or Firm*—Chas. W. Rummler

[57] ABSTRACT

A new pot chrysanthemum cultivar originated as a sport of the variety "Spirit" (U.S. Plant Pat. No. 3,813) and distinguished by its white hemispherical blooms which have serrate-tipped ray florets and which are somewhat smaller in diameter than the blooms of the parent plant. The new plant is generally similar to its parent in growth habit but is slightly shorter in average height.

4 Drawing Figures

BACKGROUND OF THE NEW PLANT

This new chrysanthemum variety was discovered by me in November 1976 among a group of the variety "Spirit" (U.S. Plant Pat. No. 3,813) being grown in greenhouse at West Chicago, Ill., in connection with work being carried on with the object of developing new and improved chrysanthemum varieties for the commercial market. Because of the novel characteristics of the blooms of this sport, it was reproduced by me by means of cuttings and subsequent propagation of this new plant by vegetative cuttings has shown that its novel characteristics hold true from generation to generation and appear to be firmly fixed. Commercial propagation of this new variety is now being carried on at Cortez, Fla., and at West Chicago, Ill.

DESCRIPTION OF THE DRAWINGS

My new chrysanthemum plant is illustrated by the accompanying drawings, one sheet of which is a photographic view made in June 1978 at West Chicago, Ill., showing a potted plant in full bloom and in full color, and the second sheet is a print of a machine copy of typical leaves of the new plant at several stages of maturity.

DESCRIPTION OF THE NEW PLANT

The following is a detailed description of my new chrysanthemum variety with color designations according to The R.H.S. Colour Chart published by The Royal Horticultural Society of London, England.

THE PLANT

Origin: Sport.

Parentage: "Spirit" (U.S. Plant Patent 3,813).

Classification:

*Botanic.*—*Chrysanthemum morifolium.*

*Commercial.*—Greenhouse pot plant.

Form: Perennial herbaceous bush.

Height: 24 to 31 cm.

Growth: Terminal, vigorous and upright, sturdy and with good strength.

Branching: Sturdy and strong under normal conditions.

Foliage: Quantity — abundant with 7 to 9 leaves on about 10 cm. of stem length.

*Leaf size.*—Length — about 4.7 to 8.5 cm. Width — about 2.7 to 5.5 cm.

*Leaf shape.*—Lobed, lanceolate and slightly serrated.

*Surface aspect.*—Canescent.

*Color.*—Upper side — 147A. Under side — 147B.

*Venation.*—Pinnate.

*Petioles.*—Length — about 0.09 to 2.0 cm.

THE BUD

Form: Globular.

Size: About 1.2 to 1.4 cm. in diameter and about 0.8 to 1.0 cm. in depth.

Opening rate: The bud opens slowly.

Color:

*When phyllaries first divide.*—145B.

*When florets begin to unfurl.*—8D.

Phyllaries: The outside of the receptacle has many involucral bracts which are upstanding and spear-shaped.

*Color.*—Inside — 137A. Outside — 137B.

*Surface aspect.*—Pubescent.

Peduncle: Strong and erect.

*Length.*—About 1.2 to 1.6 cm.

*Surface aspect.*—Pubescent.

THE FLOWER

Flowering capability: This plant can be flowered the year around with photoperiod control.

Recommended flowering:

*Northern U.S.*—March through November.

*Southern U.S.*—Year around.

Natural flowering season: October 25 to November 2.

Blooms:

*Flower type.*—Composite and novelty.

*Size.*—Medium. Diameter — about 9.0 to 9.5 cm. Depth — about 5.0 to 6.0 cm.

*Borne.*—Singly when disbudded and in multiples when grown as spray plant.

*Shape.*—When bloom first opens — cup-shaped. As bloom matures — becomes hemispherical in form.

Florets: Number — Numerous.

*Form.*—Novelty.

| Color: | May | June |
|---|---|---|
| Outer florets: | | |
| Upper side- | 155D | 155D |
| Reverse side- | 155D | 155D |
| Inside florets: | | |
| Upper side- | 155D and 11D | 155D and 11D |
| Reverse side- | 155D and 11D | 155D and 11D |

*Tonality at a distance of about* 2 *meters.*—Between 155D and 11D.

*Firmness.*—Medium.

*Appearance.*—Very slightly shiny.

*Discoloration.*—None.

*Persistence.*—The florets hang on and dry.

Peduncle: Sturdy and upright.

*Length.*—About 1.2 to 1.6 cm.

*Color.*—147B.

Fragrance: Typical chrysanthemum.

Lasting quality:

*On plant.*—3 weeks.

*As a cut flower.*—Not recommended for cut flower use.

REPRODUCTIVE ORGANS

Stamens: Number — 5. Arrangement — Syngenesious.

*Filaments.*—Length — about 2 to 4 mm.

*Color.*—Light yellow.

*Pollen.*—Color — yellow.

Pistils: Number — 1 to each ray and disc floret.

*Styles.*—Length — about 4 to 6 mm.

*Stigma.*—Color — yellow.

Ovaries: Inferior, bicarpellate.

This new cultivar of potted chrysanthemum is particularly characterized in uniqueness, when compared to the parent variety "Spirit", by its serrate-tipped ray florets, by its blooms which average about 1.6 cm. smaller diameter than those of the parent, and by its shorter plant habit which averages about 3 cm. less in height than its parent.

I claim:

1. A new and distinct potted chrysanthemum cultivar, substantially as herein shown and described, particularly characterized by the serrate-tipped ray florets of its generally hemispherically shaped blooms.

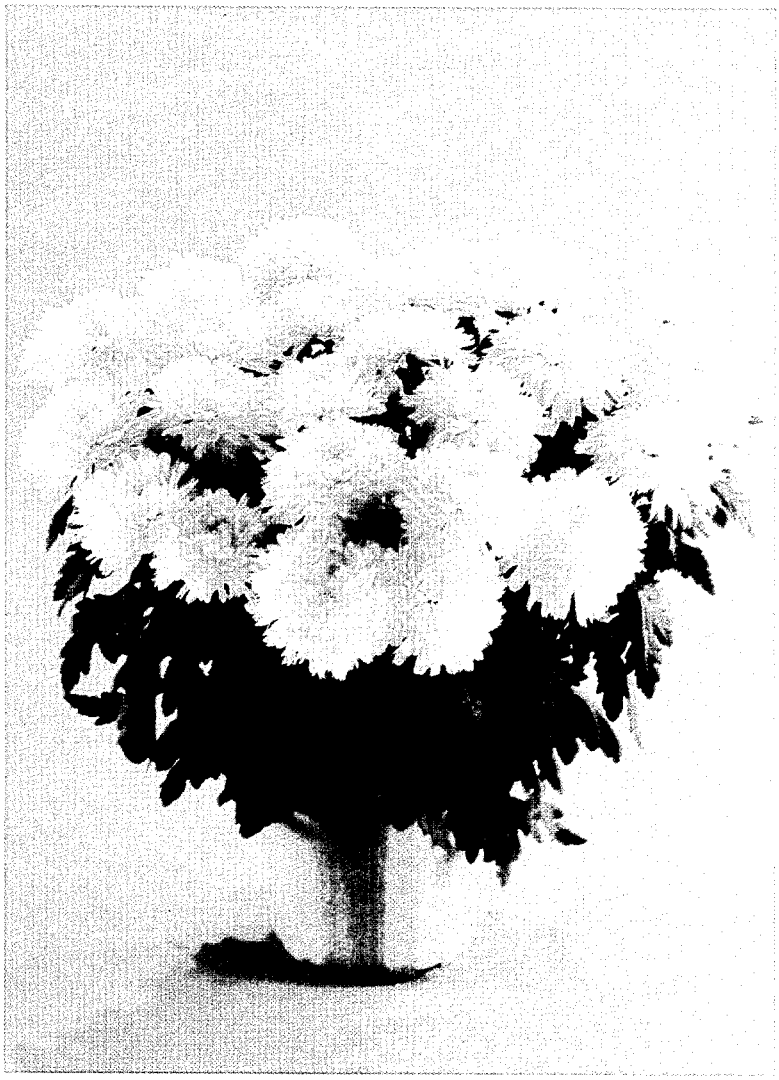

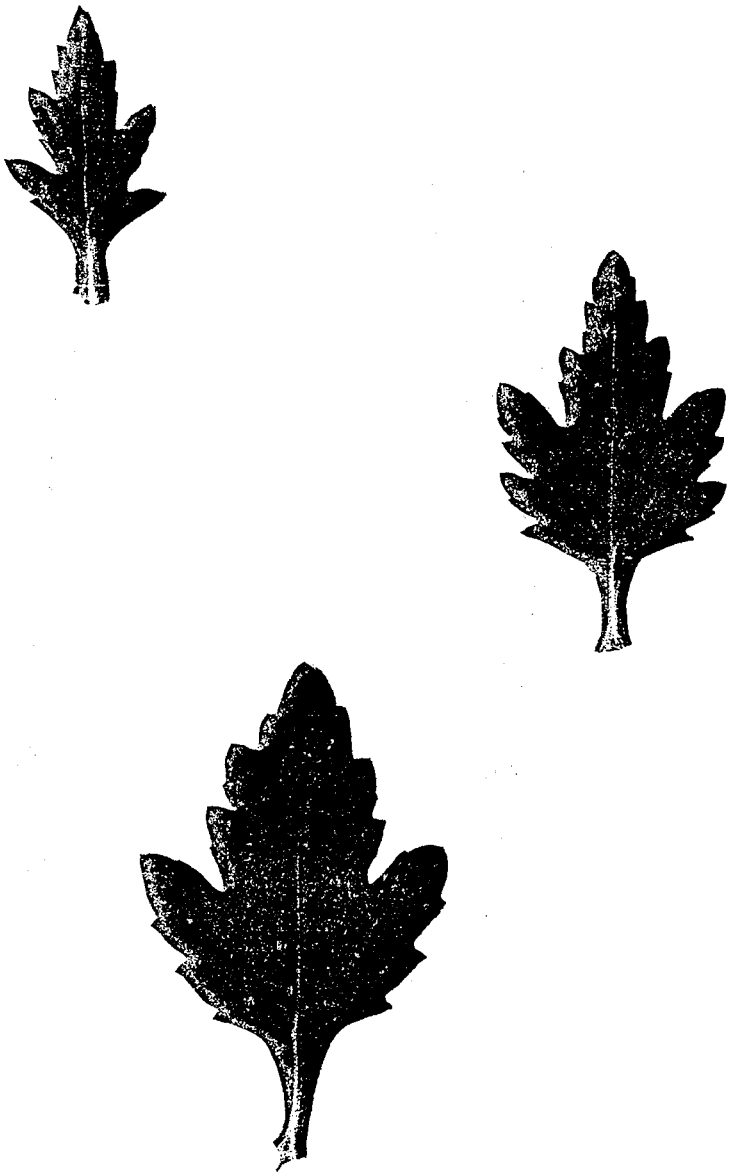

* * * * *